United States Patent [19]

Ghaoui

[11] Patent Number: 4,960,444
[45] Date of Patent: Oct. 2, 1990

[54] METHOD FOR THE DETERMINATION OF ORGANIC ACIDS IN AN AQUEOUS SAMPLE BY; GAS CHROMATOGRAPHY

[75] Inventor: Labib Ghaoui, Midland, Mich.

[73] Assignee: The Dow Chemical Company, Midland, Mich.

[21] Appl. No.: 412,954

[22] Filed: Sep. 26, 1989

[51] Int. Cl.$^5$ .............................................. B01D 15/08
[52] U.S. Cl. ........................................... 55/67; 55/197; 55/386
[58] Field of Search ............................ 55/67, 197, 386; 73/23.1; 210/198.2, 198.3

[56] References Cited

U.S. PATENT DOCUMENTS

| | | | |
|---|---|---|---|
| 3,169,390 | 2/1965 | Roper, Jr. | 55/67 X |
| 3,559,376 | 2/1971 | Emery et al. | 55/67 |
| 3,580,843 | 5/1971 | Salyer et al. | 55/67 X |
| 3,666,792 | 5/1972 | Langer | 55/67 X |
| 3,808,125 | 4/1974 | Good | 55/67 X |
| 3,822,530 | 7/1974 | Fuller et al. | 55/67 |
| 4,135,892 | 1/1979 | Coupek et al. | 55/67 |
| 4,245,005 | 1/1981 | Regnier et al. | 55/67 X |

FOREIGN PATENT DOCUMENTS

| | | | |
|---|---|---|---|
| 0264860 | 2/1989 | German Democratic Rep. | 55/386 |
| 47-016563 | 2/1972 | Japan | 55/67 |
| 52-017086 | 2/1977 | Japan | 55/386 |

OTHER PUBLICATIONS

J. Strassburger et al., "Analysis of Methyl Methacrylate Copolymers by Gas Chromatography", Analytical Chemistry, vol. 32, No. 4, Apr. 1960, pp. 454 and 455.
Anspec Gas Chromatography Supplies & Accessories Catalog #14.
W. Jennings, *Gas Chromatography with Glass Capillary Columns*, 2nd Ed., pp. 39–47 (1980).

*Primary Examiner*—Robert Spitzer
*Attorney, Agent, or Firm*—Timothy S. Stevens

[57] ABSTRACT

A gas chromatography method for the determination of organic acids using an otherwise conventional gas chromatography system, the advance being injecting a predetermined volume of an aqueous sample containing the organic acids for separation in a gas chromatography column having a polycarbonate resin stationary phase. The use of the polycarbonate resin stationary phase results in a method more resistant to the development of tailing peaks and other problems than the use of prior stationary phases. The method is especially beneficial for determining acrylic acid monomer in mixtures of acrylamide monomer and water.

9 Claims, 1 Drawing Sheet

METHOD FOR THE DETERMINATION OF ORGANIC ACIDS IN AN AQUEOUS SAMPLE BY; GAS CHROMATOGRAPHY

BACKGROUND OF THE INVENTION

Gas Chromatography is an important and well developed technique of chemical analysis. Generally, in the Gas Chromatography technique a small aliquot of a sample containing several volatile components of interest dissolved in a volatile solvent is evaporated into a stream of mobile phase gas. This gas stream is then flowed past a relatively nonvolatile stationary phase and finally to a detector. The components of interest partition between the stationary phase and the mobile phase gas. If the partition coefficients of the components of interest are sufficiently different, then the components of interest are separated along the stationary phase. The separated components of interest are then detected and recorded as separate peaks on a chromatogram. The stationary phase can be coated on specially processed diatomaceous silica particles which are then packed into a tube to make a classical packed gas chromatography column. The stationary phase can also be coated on the interior wall of a capillary tube to make a capillary gas chromatography column. A large variety of materials have been used as the stationary phase in Gas Chromatography including lubricating oils and greases, waxes, polyesters, silicone oils, styrene polymers and LEXAN brand polycarbonate resin from General Electric.

The determination of organic acids in aqueous samples by Gas Chromatography is a problem for the gas chromatographer. The chromatography column deteriorates with repeated injections which causes the chromatographic peaks of the acids to tail and interferes with accurate quantitation of the acids. These problems are caused by the relatively high polarity of the organic acids and the effects of water and nonvolatile residues of the sample on the stationary phase and the stationary phase support. In the face of these problems, most gas chromatographers derivatize the organic acids to make methyl esters of them for injection into the gas chromatograph. Derivatizing the organic acids converts them into less polar compounds dissolved in a nonaqueous volatile organic solvent. However, derivatizing a sample is time consuming and expensive. It would be an advance in the art of Gas Chromatography if a stable method were developed wherein the organic acids in an aqueous sample could be determined without the need to derivatize them.

SUMMARY OF THE INVENTION

The present invention is an improved Gas Chromatography method for the determination of organic acids in an aqueous sample without the need to derivatize the sample. The method generally includes the steps of evaporating the organic acids into a stream of mobile phase gas, flowing the mobile phase gas and evaporated organic acids past a gas chromatography stationary phase disposed in a gas chromatography column to separate the organic acids and then flowing the mobile phase gas and separated organic acids to a detector to generate a chromatogram, wherein the improvement of the present invention comprises two steps. The first step is to evaporate a predetermined volume of an aqueous sample of the organic acids into the flowing stream of mobile phase gas flowing into the gas chromatography column. The second step is to flow the mobile phase gas and evaporated sample through the gas chromatography column having a stationary phase that comprises polycarbonate resin so that the organic acids are separated in the column. The present invention can be used to analyze many samples without significant peak tailing or loss of accuracy.

DETAILED DESCRIPTION OF THE INVENTION

Figure 1:
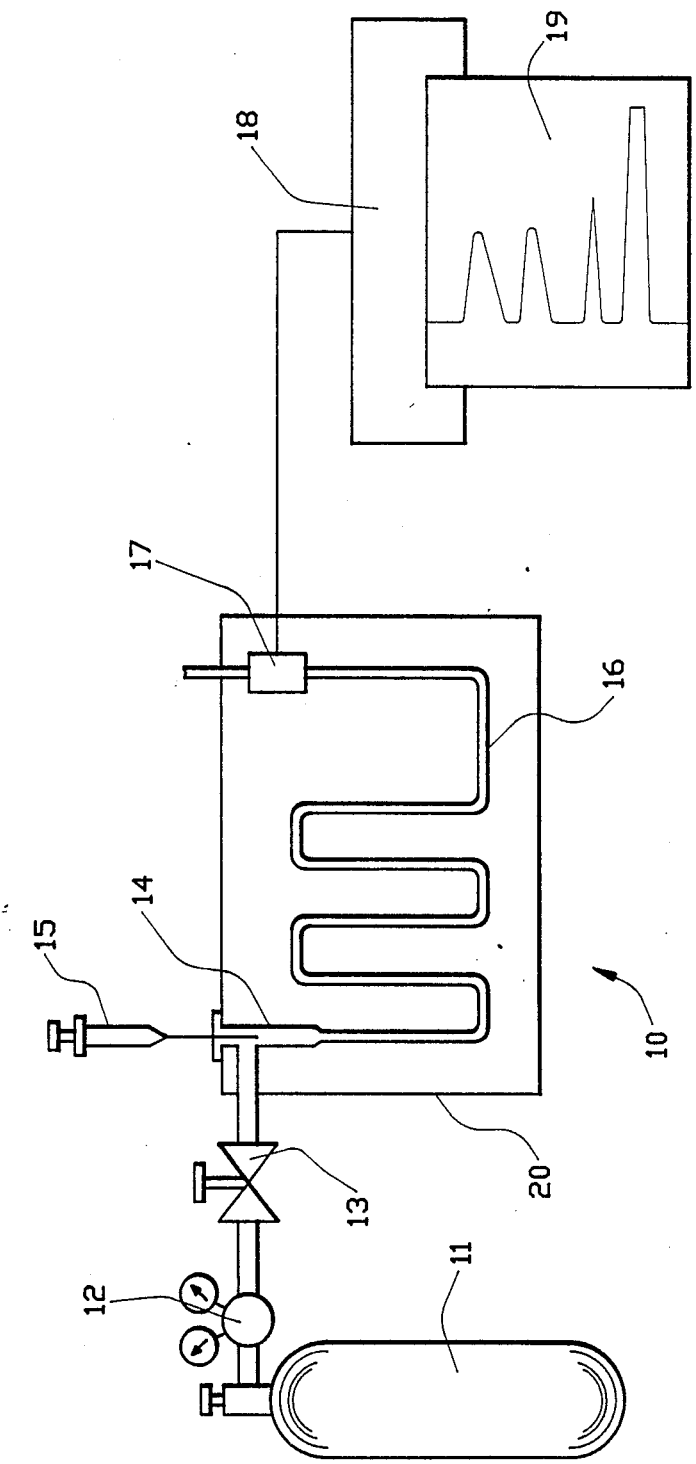
FIG. 1 shows a schematic drawing of a gas chromatography system being used to practice the present invention.

Referring now to FIG. 1, therein is shown a gas chromatography system 10 suitable to practice the present invention including a tank of compressed helium gas 11 as the source of mobile phase gas for the system 10. A regulator valve 12 is used to control the pressure of the mobile phase gas to a flow control valve 13 which controls the flow of mobile phase gas through the system 10. The flow control valve 13 is connected to a sample injector 14. A predetermined volume of a sample containing three volatile components of interest dissolved in a volatile solvent is introduced into the injector 14 by the use of a syringe 15. One end of a gas chromatography column 16 is connected to the injector 14. The other end of the gas chromatography column 16 is connected to a detector 17. The detector 17 is connected to a strip chart recorder 18. An oven 20 is used to control the temperature of the column 16. The predetermined volume of sample injected by the syringe 15 is evaporated in the injector 14 and carried into the column 16 by the flow of the carrier gas. The column 16 contains a gas chromatography stationary phase and the partition coefficient of the solvent and the three components of interest between the stationary phase and the mobile phase is sufficiently different so that each emerges from the column 16 at a different time. The detector 17 senses the separated components of interest and the solvent as they pass through it and the recorder 18 draws a chromatogram 19 showing a tall off-scale solvent peak and three on-scale peaks for the three separated components of interest.

The description in the previous paragraph is to a conventional gas chromatography system. The improvement of the present method is to use the following two steps with such a system. The first step is to evaporate a predetermined volume of an aqueous sample containing at least one organic acid into the mobile phase gas stream. In the system 10 this is done by injecting a predetermined volume of such a sample into the injector 14 using the syringe 15. The specific type of injection used in the present invention is not critical and can be on-column, split, splitless and flash injection, manual or automatic, valve and syringe. An aqueous sample is a sample that contains at least one percent water by weight. However, the relative benefits of the present invention are greater when the sample contains more water such as ten, twenty, or forty percent water by weight. The maximum relative benefits of the present invention are obtained when the sample contains more than about eighty percent water by weight. This is because in conventional gas chromatography systems water and nonvolatile residue tends to cause a deterioration of the stationary phase and stationary phase support of the gas chromatography column as evidenced by peak tailing that can be serious after relatively few injections. For example, when the sample contains water, acrylonitrile and acrylic acid, about ten injections can be made when a polar stationary phase is used, e.g., DEGS, and about twenty injections can be made when a non-polar stationary phase is used, e.g., SP-1000. In contrast, the present method can be used for many more than twenty injections of this demanding sample, see Example 2 below.

An organic acid is a carboxylic acid (such as acrylic acid, acetic acid, propionic acid, and decanoic acid) or a sulfonic acid (such as methane sulfonic acid, ethane sulfonic acid, ethyl benzene sulfonic acid, 4-ethylbenzene sulfonic acid and p-toluene sulfonic acid).

The second step of the present invention is to flow the mobile phase gas and evaporated sample through a gas chromatography column having a stationary phase comprising polycarbonate resin so that the organic acids are chromatographically separated in the column. The type of column used is not critical in the present invention as long as the stationary phase comprises a polycarbonate resin and can include wall-coated open tubes (conventional capillary columns), support coated open tubes, classical packed columns, and packed capillary columns. The most preferred column type is the wall-coated open tube type being in length more than one meter but less than one hundred meters, having an internal diameter of more than one hundred micrometers but less than six hundred micrometers, and having a stationary phase coating thicker than one thousand angstroms but thinner than ten microns in a fused silica capillary column coated according to the static coating technique of Walter Jennings as described in his book entitled Gas Chromatography With Glass Capillary Columns, 2nd Ed., on pages 39 and 40. However, it should be understood that this specific stationary phase coating technique is not critical in the present invention.

Polycarbonate resins are commercially available, e.g., from the Dow Chemical Company and from the General Electric Company. Polycarbonate resins usually are commercially derived from bisphenol A and phosgene. The following three structural variants of polycarbonate resins are preferred representative examples:

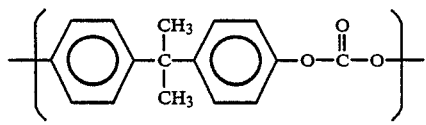

Structure 1

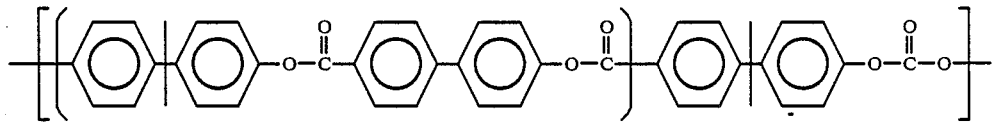

Structure 2

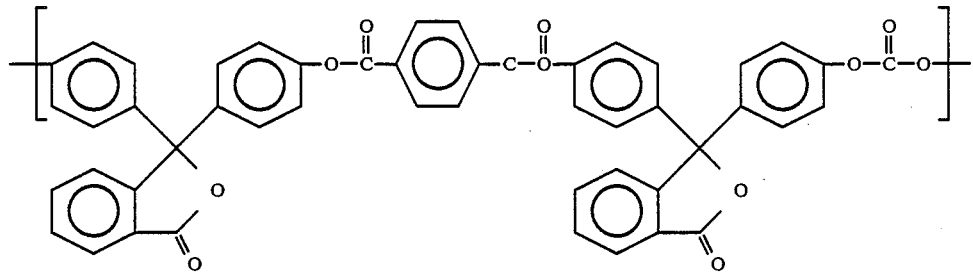

Structure 3 wherein each structure is a structural polymer unit of a polycarbonate resin.

Structure 2 above is commercially available from The Dow Chemical Company as Product Code C8700297-1521.

In the present invention it is most preferable that the stationary phase consist essentially of a polycarbonate resin. It should be understood that the stationary phase used in the present invention can be cross-linked, e.g., by using peroxides as is well understood in the art, and that the use of such a cross-linked stationary phase is included within the scope of the present invention. One of the benefits of a cross-linked stationary phase is that it can be washed with a wide variety of solvents without stripping the stationary phase from the column whereas a noncross-linked stationary phase can not readily be washed with a solvent that dissolves it.

As discussed above, the present method is applicable for the general determination of organic acids in an aqueous sample. However, one specific application where the present method is believed to be the method of choice is the determination of acrylic acid monomer in acrylamide monomer/water solutions as discussed in detail in Example 2 below. This analysis is difficult by conventional gas chromatography.

EXAMPLE 1

A ten and one tenth meter long section of 250 micrometer internal diameter fused silica capillary tubing is cut from a stock roll of this tubing. Forty milligrams of Dow C8700297-1521 polycarbonate thermoplastic resin is dissolved in ten milliliters of methylene chloride to make a polycarbonate solution. The polycarbonate solution is then flowed into one end of the section of capillary tubing at a pressure of five pounds per square inch. The other end of the tubing, with the polycarbonate solution dripping from it, is then immersed into melted paraffin wax at eighty to one hundred degrees centigrade. The flow of polycarbonate solution through the tubing is then stopped so that melted wax is back flowed into the other end of the tubing for a length of a few centimeters. The wax is then cooled to solidify it so that the other end of the tubing is sealed. The one end of the tubing is then connected to a vacuum source to evaporate the methylene chloride in the tubing to coat the inside wall of the tubing with the polycarbonate resin. Ten centimeters of the other end of the tubing is cut from the tubing to remove the wax seal.

The tubing is installed in a Hewlett Packard model 5890 gas chromatograph. Helium mobile phase gas is flowed through the tubing at a flow rate of about one cubic centimeter per minute. The oven of the gas chromatograph is programmed from fifty degrees centigrade to two hundred and eighty degrees centigrade at one degree centigrade per minute for seventeen hours to condition the tubing as a capillary gas chromatography column.

The gas chromatograph is then set for an oven program of ninety to two hundred and fifty degrees centigrade at ten degrees centigrade per minute, a helium mobile phase gas linear velocity of fourteen to twenty centimeters per second, a two hundred to one split injection at two hundred and fifty degrees centigrade using a split flow of two hundred milliliters per minute, flame ionization detection at two hundred and fifty degrees centigrade, air flow to the detector of three hundred milliliters per minute, hydrogen flow to the detector of thirty milliliters per minute, make up gas flow of twenty milliliters per minute of helium, and an injection volume of one microliter. A sample of one hundred parts per million each of C-3, C-4, C-5, C-6, C-7, C-8 and C-9 n-carboxylic acids in fifty percent acetone fifty percent water is injected. The resulting chromatogram shows an off scale acetone peak at 1.06 minutes, and the following on scale acid peaks: C-3 at 3.98 minutes; C-4 at 5.59 minutes; C-5 at 7.19 minutes; C-6 at 8.58 minutes; C-7 at 9.80 minutes; C-8 at 10.91 minutes; and C-9 at 11.92 minutes. This analysis is repeated two hundred times without the development of peak tailing in the chromatograms.

EXAMPLE 2

The same system as above is used with the following changes. The injection is changed from split injection to an on-column injection of two hundred nanoliters. The column oven temperature program is changed to an initial temperature of one hundred and twenty degrees centigrade programed to increase at eight degrees per minute. The sample is about fifty percent water and about fifty percent acrylamide monomer, this mixture also containing 1.6 percent acrylic acid monomer and 2 percent acetic acid as an internal standard. An injection of the sample is made and the resulting chromatogram shows an acetic acid peak at 1.78 minutes, an acrylic acid peak at 2.80 minutes and an acrylamide peak eluting between 4 and 9 minutes. This analysis is repeated two hundred times without the development of peak tailing in the chromatograms.

What is claimed is:

1. In a method for the determination of organic acids by gas chromatography generally including the steps of evaporating the organic acids into a stream of mobile phase gas, flowing the mobile phase gas and evaporated organic acids past a stationary phase disposed in a gas chromatography column to separate the organic acids by gas chromatography and then flowing the mobile phase gas and chromatographically separated organic acids to a detector to generate a chromatogram, wherein the improvement comprises the steps of:
    (a) evaporating a predetermining volume of an aqueous sample containing the organic acids into the flowing stream of mobile phase gas flowing into the gas chromatography column;
    (b) flowing the mobile phase gas and evaporated sample through the gas chromatography column the stationary phase of which comprises polycarbonate resin so that the organic acids are chromatographically separated in the column.

2. The method of claim 1 wherein the stationary phase is disposed on a particulate support, the support contained in the column.

3. The method of claim 1 wherein the stationary phase is disposed on the interior surface of a capillary tube.

4. The method of claim 3 wherein the stationary phase is disposed as a coating on the interior surface of a fused silica capillary tube.

5. The method of claim 4 wherein the stationary phase comprises a polycarbonate resin predominantly having the following structural unit:

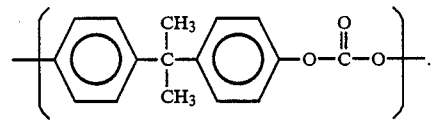

6. The method of claim 4 wherein the stationary phase comprises a polycarbonate resin predominantly having the following structural unit:

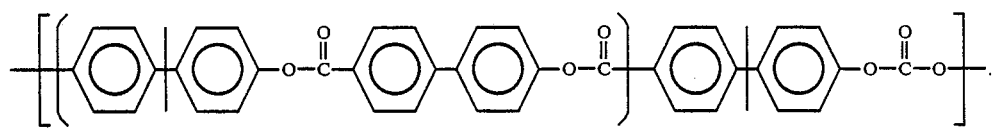

7. The method of claim 4 wherein the stationary phase comprises a polycarbonate resin predominantly having the following structural unit:

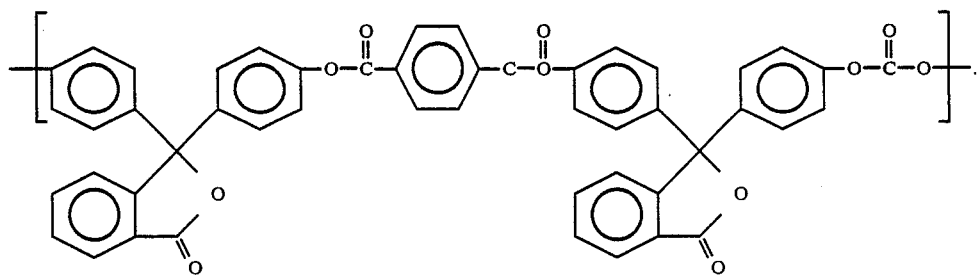

8. The method of claim 4 wherein the fused silica capillary tube is longer than one meter and shorter than one hundred meters, and wherein the fused silica capillary tube internal diameter is more than one hundred micrometers and less than six hundred micrometers, and wherein the stationary phase coating is thicker than one thousand angstroms and thinner than five micrometers, and wherein the stationary phase consists essentially of polycarbonate resin.

9. The method of claim 8 wherein the sample comprises acrylamide monomer, water and acrylic acid monomer.

* * * * *